(12) United States Patent
Xu et al.

(10) Patent No.: US 7,754,444 B2
(45) Date of Patent: Jul. 13, 2010

(54) BIOFUNCTIONAL MAGNETIC NANOPARTICLES FOR PATHOGEN DETECTION

(75) Inventors: Bing Xu, Kowloon (HK); Pak Leung Ho, Kwai Chung (HK); Hongwei Gu, Kowloon (HK)

(73) Assignee: The Hong Kong University of Science and Technology, Kowloon, Hong Kong (CN)

( * ) Notice: Subject to any disclaimer, the term of this patent is extended or adjusted under 35 U.S.C. 154(b) by 847 days.

(21) Appl. No.: 11/159,882

(22) Filed: Jun. 23, 2005

(65) Prior Publication Data
US 2006/0292555 A1    Dec. 28, 2006

Related U.S. Application Data (60) Provisional application No. 60/582,700, filed on Jun. 24, 2004.

(51) Int. Cl.
*C12Q 1/70* (2006.01)
*C12Q 1/04* (2006.01)
(52) U.S. Cl. .............................. 435/34; 435/5; 977/900
(58) Field of Classification Search .................... 435/5, 435/34
See application file for complete search history.

(56) References Cited

U.S. PATENT DOCUMENTS

| | | | |
|---|---|---|---|
| 4,590,922 A * | 5/1986 | Gordon | 600/10 |
| 5,279,936 A * | 1/1994 | Vorpahl | 435/6 |
| 6,254,662 B1 | 7/2001 | Murray et al. | |
| 6,262,129 B1 | 7/2001 | Murray et al. | |
| 6,302,940 B2 | 10/2001 | Murray et al. | |
| 6,620,627 B1 | 9/2003 | Liberti et al. | |
| 7,186,398 B2 * | 3/2007 | Andres et al. | 424/9.1 |
| 2004/0058389 A1 * | 3/2004 | Wang et al. | 435/7.1 |
| 2006/0188876 A1 * | 8/2006 | Kilaas et al. | 435/6 |

FOREIGN PATENT DOCUMENTS

| | | |
|---|---|---|
| DE | 10027607 A1 | 12/2001 |
| WO | WO 01/10558 A1 | 2/2001 |
| WO | WO 02/20825 A1 | 3/2002 |
| WO | WO 02/90565 A2 | 11/2002 |

OTHER PUBLICATIONS

Pankhurst et al. 2003. Applications of Magnetic Nanoparticles in Biomedicine, Journal of Physics D: Applied Physics, vol. 36, pp. R167-R181.*

Gu et al 2003. Using Biofunctional Magnetic Nanoparticles to Capture Gram-Negative Bacteria at an Ultra-low Concentration, Chem. Commun., Jul. 2003, pp. 1966-1967.*

Bukhari et al.1998. Immunomagnetic Separation of Cryptosporidium parvum from Source Water Samples of Various Turbidities. Applied and Environmental Microbiology, vol. 64, No. 11, pp. 4495-4499.*

Kronick et al. 1986. Use of superparamagnetic particles for isolation of Cells. Journal of Biochemical and Biophysical Methods, vol. 12, pp. 73-80.*

Puntes, et al. "Colloidal Nanocrystal Shape and-Size Control: The Case of Cobalt" Science 2001, vol. 291, 2115-2117.

Weller, et al. "Thermal Effect Limits in Ultrahigh-Density Magnetic Recording" IEEE Transactions on Magnetics 1999, vol. 35, 4423-4439.

Osterloh, F.E. "Solution Self-Assembly of Magnetic Light Modulators from Exfoliated Perovskite and Magnetite Nanoparticles" J. Am. Chem. Soc. 2002, vol. 124, 6248-6249.

Zhang, et al. "Temperature Dependence of cation Distribution and Oxidation State in Magnetic Mn-Fe Ferrite Nanocrystals" J. Am. Chem. Soc. 1998, vol. 120, 1800-1804.

Tripp, et al. "Self-Assembly of Cobalt Nanoparticle Rings" J. Am. Chem. Soc. 2002, vol. 124, 7914-7915.

Park, et al. "Synthesis of 'Solid Solution' and 'Core Shell' Type Cobalt-Platinum Magnetic Nanoparticles via Transmetalation Reactions" J. Am. Chem. Soc. 2001, vol. 123, 5743-5746.

Majetich, et al. "Preparation and Properties of Carbon-Coated Magnetic Nanocrystallites" Physical Review B 1993, vol. 48, 16845-16848.

(Continued)

*Primary Examiner*—Jon P Weber
*Assistant Examiner*—Kailash C Srivastava
(74) *Attorney, Agent, or Firm*—George G. Wang; Wilkinson & Grist (57) ABSTRACT

This invention provides a method of detecting pathogens comprising the steps of: (a) contacting a sufficient amount of biofunctional magnetic nanoparticles with an appropriate sample for an appropriate period of time to permit the formation of complexes between the pathogens in the sample and the nanoparticles; (b) using a magnetic field to aggregate said complexes; and (c) detecting said complexes. The method may further comprise the additional step of removing said complexes. The biofunctional magnetic nanoparticles are preferably a conjugate of vancomycin and FePt. The pathogens may be bacteria or viruses, and the sample may be a solid, liquid, or gas. Detection may involve conventional fluorescence assay, enzyme-linked immunosorbent assay (ELISA), optical microscope, electron microscope, or a combination thereof. The sensitivity of detection for the method is at least as low as 10 colony forming units (cfu) of the pathogens in one milliliter of solution within one hour.

13 Claims, 9 Drawing Sheets

OTHER PUBLICATIONS

Sun, et al. "Polymer Mediated Self-Assembly of Magnetic Nanoparticles" J. Am. Chem. Soc. 2002, vol. 124, 2884-2885.

Sun, et al. "Monodisperse FePt Nanoparticles and Ferromagnetic FePt Nanocrystal Superlattices" Science 2000, vol. 287, 1989-1992.

Josephson, et al. "Near-Infrared Fluorescent Nanoparticles as Combined MR/Optical Imaging Probes" Bioconjugate Chem. 2002, vol. 13, 554-560.

Perez, et al. "DNA-Based Magnetic Nanoparticle Assembly Acts as a Magnetic Relaxation Nanoswitch Allowing Screening of DNA-Cleaving Agents" J. Am. Chem. Soc. 2002, vol. 124, 2856-2857.

Josephson, et al. "Magnetic Nanosensors for the Detection of Oligonucleotide Sequences" Angew. Chem. Int. Ed. 2001, vol. 40, 3204-3206.

Dyal, et al. "Activity of *Candida rugosa* Lipase Immobilized on gamma-Fe2O3 Magnetic Nanoparticles" J. Am. Chem. Soc. 2003, vol. 125, 1684-1685.

Lewin, et al. "Tat Peptide-Derivatized Magnetic Nanoparticles Allow in Vivo tracking and Recovery of Progenitor Cells" Nature Biotechnology 2000, vol. 18, 410-414.

Safarik, et al. "Magnetic Nanoparticles and Biosciences", Monatschefte fur Chemie 2002, vol. 133, 737-759.

Perez, et al. "Viral-Induced Self-Assembly of Magnetic Nanoparticles Allows the Detection of Viral Particles in Biological Media" J. Am. Chem. Soc. 2003, vol. 125, 10192-10193.

Mammen, et al. "Polyvalent Interactions in Biological Systems: Implications for Design and Use of Multivalent Ligands and Inhibitors" Angew. Chem. Int. Ed. 1998, vol. 37, 2754-2794.

Xing, et al. "Hydrophobic Interaction and Hydrogen Bonding Cooperatively Confer a Vancomycin Hydrogel: A Potential Candidate for Biomaterials" J. Am. Chem. Soc. 2002, vol. 124, 14846-14847.

Rao, et al. "Using Surface Plasmon Resonance to Study the binding of Vancomycin and its Dimer to Self-Assembled Monolayers Presenting D-Ala-D-Ala" J. Am. Chem. Soc. 1999, vol. 121, 2629-2630.

Rao, et al. "A Trivalent system from Vancomycin.D-Ala-D-Ala with Higher Affinity than Avidin.Biotin" Science 1998, vol. 280, 708-711.

Gu, et al. "Chemical Synthesis of Narrowly Dispersed SmCo5 Nanoparticles" Journal of Applied Physics 2003, vol. 93, 7589-7591.

Gu, et al. "Presenting Vancomycin on Nanoparticles to Enhance Antimicrobial Activities" Nano Letters 2003, vol. 3, 1261-1263.

Wagner, et al. "Evaluation of an automated microbiologic blood culture for detection of bacteria in platelet components" Transfusion 1998, vol. 38, 674-679.

Cha, et al. "Rapid detection of *Salmonella typhimurium* in chicken carcass wash water using the Immunoelectrochemical method" J. Food Protection 2000, vol. 63, 1043-1048.

Walsh, C. "Deconstructing vancomycin" Science 1999, vol. 284, 442-443.

Fan, et al. "Vancomycin resistance: structure of D-Alanine;D-Alanine ligase at 2.3 A Resolution" Science 1994, vol. 266, 439-443.

Walsh, C. "Antibiotics: actions, origins, resistance" 1st ed.; ASM press: Washington, D.C., 2003; pp. 143-155.

Gu, et al. "Using Biofunctional Magnetic Nanoparticles to Capture Vancomycin-Resistant Enterococci and Other Gram-Positive Bacteria at Ultralow Concentration" J. Am. Chem. Soc. 2003, vol. 125, 15702-15703.

Gu, et al. "Using Biofunctional Magnetic Nanoparticles to Capture Gram-Negative Bacteria at An Ultra-low Concentration" Chem. Comm. 2003, 1966-1967.

* cited by examiner

—Linker—FG          Linker: e.g.,

Mangetic nanoparticles (< 20 nm)          Function group (FG): Vancomycin, antibiotics, ligands, receptors, metal complex, etc.
e.g., FePt, SmCo$_5$, Fe$_3$O$_4$, Fe$_2$O$_3$, etc one or more copies of -linker-FG covalently bond to magnetic nanoparticles

CNS
6 cfu/ml

Strept. pneumoniae
4 cfu /ml control

BIOFUNCTIONAL MAGNETIC NANOPARTICLES FOR PATHOGEN DETECTION

This application claims the benefit of U.S. Ser. No. 60/582,700, filed Jun. 24, 2004, the contents of which are incorporated herein in its entirety by reference.

Throughout this application, various references are cited and disclosures of these publications in their entireties are hereby incorporated by reference into this application in order to more fully describe the state of the art to which this invention pertains.

BACKGROUND OF THE INVENTION

Instant and sensitive detection of pathogens (e.g., bacteria, viruses) at ultra-low concentrations without time consuming procedures, such as incubation or amplification by polymerase chain reaction (PCR) offers obvious clinical benefits. However, there are, to date, no general and satisfactory assays that can detect bacteria at concentrations of <$10^2$ colony forming units per milliliter (cfu/mL) without pre-enriching the bacteria via a culture process. [1]

Compared to magnetic beads (1-5 μm in diameter) used in biological separations, magnetic nanoparticles[2,3] (less than 10 nm in diameter) promise high-performance because of their large surface/volume ratios and easy entry into cells. [4] Despite intense efforts in the study of magnetic nanoparticles, the application of magnetic nanoparticles in biomedicine is just emerging. [5]

SUMMARY OF THE INVENTION

The present invention discloses a method of detection of microorganisms, such as pathogens, at ultra-low concentrations without time consuming procedures, such as culture process or polymerase chain reaction (PCR). The present invention discloses a method that uses biofunctional magnetic nanoparticles to capture and detect vancomycin-resistant enterococci (VRE) and other Gram-positive or Gram-negative bacteria at concentrations of at least as low as 10 cfu/mL within an hour, which is an order of magnitude more sensitive than the current best assay for bacteria detection based on luminescence (detection limit: 180 cfu/mL). This invention offers benefits in clinical diagnosis, food quality monitoring, environmental protection, and bioterrorism prevention.

The present invention takes advantage of the large surface/volume ratio of magnetic nanoparticles and the concept of ligand-receptor interactions for fast pathogen detection. The method combines two kinds of interactions: 1) magnetic dipole interactions that aggregate the magnetic nanoparticles under a magnetic field and 2) specific multiple ligand-receptor interactions (i.e., polyvalent interactions [6]) that offer high avidity between magnetic nanoparticles and bacteria when the ligands covalently bond to the magnetic nanoparticles.

For example, vancomycin (Van), an antibiotic, can be attached to the surface of FePt (iron-platinum) nanoparticles[3] (3-4 nm in diameter). Van can bind to the terminal peptide, D-Ala-D-Ala, on the cell wall of a Gram-positive bacterium via hydrogen bonds (FIG. 1), [7,8] and previous studies have demonstrated that multivalent Vans have high affinities toward multiple D-Ala-D-Ala receptors. [9] The designed conjugate of Van and FePt magnetic nanoparticle (FePt—Van) exhibited high sensitivity to bacteria whose cell walls express D-Ala-D-Ala as the terminal peptides, and captured those Gram-positive bacteria at a concentration as low as ~4 cfu/mL. More importantly, this invention shows that the designed conjugate of Van and FePt magnetic nanoparticle (FePt—Van) effectively captures VRE, a life-threatening pathogen, at a concentration of $10^1$-$10^2$ cfu/mL via polyvalent interactions, which cannot be done by microbeads.

After capture of the bacteria by the magnetic nanoparticles, the resulting bacteria-nanoparticle complex can be aggregated using a magnetic field. Detection can involve analysis with an optical microscope, an electron microscope, or a combination thereof. The reduction of particle size from micrometers to nanometers allows for increased sensitivity (i.e. capture of bacteria at concentrations as low as 4 cfu/ml) and specificity (i.e. capture of bacteria only).

In another embodiment, after the bacteria has been captured by the magnetic nanoparticles, a conjugate of Van and biotin (Van-Biotin) can be used to further bind to the free D-Ala-D-Ala on the surface of the bacteria. This is beneficial, because the magnetic nanoparticles will not exhaust all the D-Ala-D-Ala (or other biomarkers) on the surface of the bacteria. Thus, the free D-Ala-D-Ala (or other biomarkers) are available for binding with a second ligand, a biotin conjugate such as Van-biotin. By exploiting the interaction between biotin and avidin, the presence of the bacteria can then be easily reported using conventional fluorescence or enzyme-linked immunosorbent assays (ELISA). Although Van-biotin was the conjugate used in this embodiment, any conjugate that contains a ligand that will bind to a pathogen and a tag (e.g., biotin, which can bind to fluorescent avidin) that will bind to a fluorescent marker can be used.

DETAILED DESCRIPTION OF THE FIGURES

FIG. 2. An illustration shows the capture of bacteria by vancomycin-conjugated magnetic nanoparticles in 2A via multivalent interaction and the corresponding control experiment in 2B.

FIG. 3. An optical image 3A and a SEM image 3C show the aggregates of *S. aureus* and Van-FePt nanoparticles; an optical image 3B and a SEM image 3D show the aggregates of control FePt nanoparticles after mixing with *S. aureus*; SEM image 3E shows the aggregates of coagulase negative staphylococci (CNS) and Van-FePt nanoparticles; and SEM image 3F shows *S. epidermidis* and Van-FePt nanoparticles (magnification for a and b=400, scale bars=1 μm; the exact counts of the bacteria were confirmed by back titration).

FIG. 4. SEM images are shown of *E. faecalis* (ATCC 29212, a Van-sensitive strain, 26 cfu/mL) in 4A, *E. GALL* (a VanC strain, 84 cfu/mL) in 4B, *E. faecium* (a VanB strain, 22 cfu/mL) in 4C, and *E. faecium* (a VanA strain, 34 cfu/mL) in 4D and the aggregates of Van-FePt nanoparticles (scale bars=1 μm, the genotypes of the strains were determined by PCR, and the exact counts of the bacteria were confirmed by back titration).

FIG. 5. SEM images are shown of the aggregate of Van-FePt nanoparticles (scale bar=1 μm) in 5A and the aggregate of Van-FePt nanoparticles and *S. epidermidis* (indicate by the arrow, scale bar=2 μm) in 5B.

FIG. 6. SEM images are shown of the aggregates of *E. coli* and Van-FePt nanoparticles (arrow indicates the *E. coli*) in 6A and the aggregates of control FePt nanoparticles in 6B. TEM images are shown of aggregates of *E. coli* and Van-FePt nanoparticles (arrow indicates the *E. coli*) in 6C and aggregates of control FePt nanoparticles in 6D.

DETAILED DESCRIPTION OF THE INVENTION

This invention provides a method of detecting microorganisms comprising steps of: (a) contacting a sufficient amount of biofunctional magnetic nanoparticles with an appropriate sample for an appropriate period of time to permit the formation of complexes between the microorganisms and nanoparticles; (b) using a magnetic field to aggregate said complexes; and (c) detecting said complexes.

The sensitivity of detection for the method is at least as low as 10 colony forming units (cfu) of the microorganisms in one milliliter of solution. On the upward end, the method of the present invention is capable of detecting anywhere from about 20, 40, 60, 80, or 100 cfu/mL. For viruses, the method of the present invention is capable of detecting concentrations at least as low as 10 plaque forming units per one milliliter of solution (pfu/mL) and upwards of about 100, 500, or 1000 pfu/mL.

In one embodiment, the microorganisms are pathogens. As used herein, pathogens are defined as any disease-producing microorganism. Pathogens include, but are not limited to, bacteria, viruses, mycoplasma, algae, amoeba, or other single-cell organisms. The bacteria may be either Gram positive or Gram negative, which may be captured at the same time by the present invention. The bacteria used in the present invention include, but are not limited to, *Staphylococcus aureus, Staphylococcus epidermidis*, coagulase negative staphylococci (CNS), *E. coli*, or Vancomycin Resistant Enterococci (VRE).

The sample to be tested can be a clinical sample, which may include, but is not limited to, bodily fluid samples, smear samples, or swab samples. The sample can also be taken from the environment, which may include, but is not limited to, water, air, or soil. The methods of pathogen detection and reduction, as discussed herein, may be applied to the residual components of bioterrorist chemical devices.

Additionally, the sample can be taken from food products, which may include, but is not limited to, liquid or solid foods that processed, concentrated, or otherwise artificially modified. The present invention can be very beneficial to the food industry where sensitive detection of pathogens is desired. Samples, whether in solid, liquid, or gas form, can be prepared accordingly (e.g. dilution, dissolution, immersion) so as to render them in solution form for use in the present invention.

As used herein, biofunctional means the ability to engage in ligand-receptor, antibody-antigen, ionic, or metal-ligand interaction. Thus, biofunctional describes the types of specific interactions possible between the magnetic nanoparticles and microorganisms in the sample. The biofunctional magnetic nanoparticles are a conjugate of magnetic nanoparticles and a functional group.

The magnetic nanoparticles may be composed of, but are not limited to, iron, noble metals (such as gold, silver, platinum, or palladium), cobalt, metal oxides, nickel, or alloys thereof. In one embodiment, the magnetic nanoparticles are iron-platinum (FePt), SmCo$_5$, Fe$_3$O$_4$, Fe$_2$O$_3$, FePd, CoPt, Sm$_x$Co$_y$@Fe$_2$O$_3$, Sm$_x$Co$_y$@Fe$_3$O$_4$, M@Fe$_2$O$_3$, or M@Fe$_3$O$_4$, whereby x=1 to 4, y=5 to 20, and M is a magnetic metal selected from the group consisting of cobalt, nickel, iron, and magnetic alloys thereof. In the embodiment described above involving Sm$_x$Co$_y$@Fe$_2$O$_3$, Sm$_x$Co$_y$@Fe$_3$O$_4$, M@Fe$_2$O$_3$, and M@Fe$_3$O$_4$, the symbol "@" merely indicates that the magnetic nanoparticles have a Sm$_x$Co$_y$ or M core and a Fe$_2$O$_3$ or Fe$_3$O$_4$ shell. Metals which can be magnetic are well known in the art. See *Magnetic Nanoparticles Having Passivated Metallic Cores*, U.S. Ser. No. 10/355,162, filed on Jan. 31, 2003, published on Oct. 9, 2003. The functional group may be an antibiotic, ligand, receptor, or metal complex. In on embodiment, the antibiotic is vancomycin (Van).

After capture of the bacteria by the magnetic nanoparticles, the resulting bacteria-nanoparticle complex can be aggregated using a magnetic field. Detection can involve analysis with an optical microscope, an electron microscope, or a combination thereof. The reduction of particle size from micrometers to nanometers allows for increased sensitivity (i.e. capture of bacteria at concentrations at least as low as 10 cfu/mL and at least as low as 4 cfu/mL for Gram positive bacteria) and specificity (i.e. capture of bacteria only).

In another embodiment, after the bacteria has been captured by the magnetic nanoparticles, a conjugate of Van and biotin (Van-Biotin) can be used to further bind to the free D-Ala-D-Ala on the surface of the bacteria. This is beneficial, because the magnetic nanoparticles will not exhaust all the D-Ala-D-Ala (or other biomarkers) on the surface of the bacteria. Thus, the free D-Ala-D-Ala (or other biomarkers) are available for binding with a second ligand, a biotin conjugate such as Van-biotin. A magnetic field can then be used to aggregrate the resulting complexes. By exploiting the interaction between biotin and avidin via an avidin-FITC (fluorescein isothiocyanate) conjugate, the presence of the bacteria can then be easily reported using conventional fluorescence or enzyme-linked immunosorbent assays (ELISA). Detection may further comprise analysis with an optical microscope, an electron microscope, or a combination thereof.

The present invention also provides a method of reducing the amount of pathogens in a sample, comprising the steps of (a) contacting a sufficient amount of biofunctional magnetic nanoparticles with an appropriate sample for an appropriate period of time to permit the formation of complexes between the pathogens and magnetic nanoparticles; and (b) using a magnetic field to aggregate said complexes; and (c) removing said complexes, thereby reducing the amount of said pathogen in the sample.

Additionally, the present invention provides a method for the reduction of pathogens in the bodily fluid of a subject in need of treatment thereof, comprising the steps of (a) obtaining bodily fluid from said subject; (b) contacting said fluid with biofunctional magnetic nanoparticles capable of binding to said pathogens under conditions permitting the formation of complexes between the pathogens and the magnetic nanoparticles; and (c) removing said complexes, thereby reducing the amount of pathogens in said fluid. The method may further comprise the reintroduction of said fluid back to said subject. In one embodiment, said fluid is blood.

The method of the present invention can be used to treat infections in a subject in need thereof. Particularly, this process may be adapted for ex vivo treatment. Bodily fluids from the subject can be extracted to a device containing the biofunctional magnetic nanoparticles under conditions that permit the formation of pathogen-nanoparticle complexes as described supra. After said process, the fluids may be introduced back to the subject.

In one embodiment, the subject is a mammal. Such mammal may be, but is not limited to, a dog, cat, rabbit, mouse, or human being. In another embodiment, the subject is a non-mammal, such as a bird, turtle, snake, or fish.

This invention provides for a composition capable of detecting or reducing microorganisms or in combination thereof, comprising an appropriate amount of biofunctional magnetic nanoparticles capable of binding to said microorganisms via ligand-receptor, antibody-antigen, ionic, or metal-ligand interaction. In one embodiment, the microorganisms are pathogens.

This invention also provides for a kit for detecting or reducing pathogens, comprising a compartment containing an appropriate amount of biofunctional magnetic nanoparticles capable of binding to said pathogens.

Additionally, this invention provides a device which performs the method for detecting or reducing microorganisms, comprising any of the above methods. Furthermore, a computer may be used to monitor the above-discussed methods of the present invention.

The invention can be better appreciated by reference to the Experimental Details which follow. Those ordinarily skilled in the art will readily appreciate that the specific experiments detailed are only illustrative and are not meant to limit the invention as described herein.

Experimental Details: Materials and Methods

Bacteria strains: Except ATCC 29212, the bacteria strains were obtained from clinical specimens. The *S. aureus* and CNS were isolated from blood culture of patients admitted to the Queen Mary Hospital, Hong Kong. The VRE were isolated from rectal swabs of patients admitted to Queen Mary Hospital, Hong Kong.

Establishment of the counts of the bacteria: Bacterial cells were suspended in saline and adjusted to the 0.5 McFarland standard (approximately 1 to $2 \times 10^8$ cfu/mL). Serial ten-fold dilutions were made until the desired inoculum density was reached. The actual count was determined by back titration. A sample of each inoculum was streak onto a blood agar plate. The dilution that yields 30 to 100 cfu/mL in the agar plate was counted for calculating the actual inoculum density. All tests were performed in triplicates.

Figure 1:
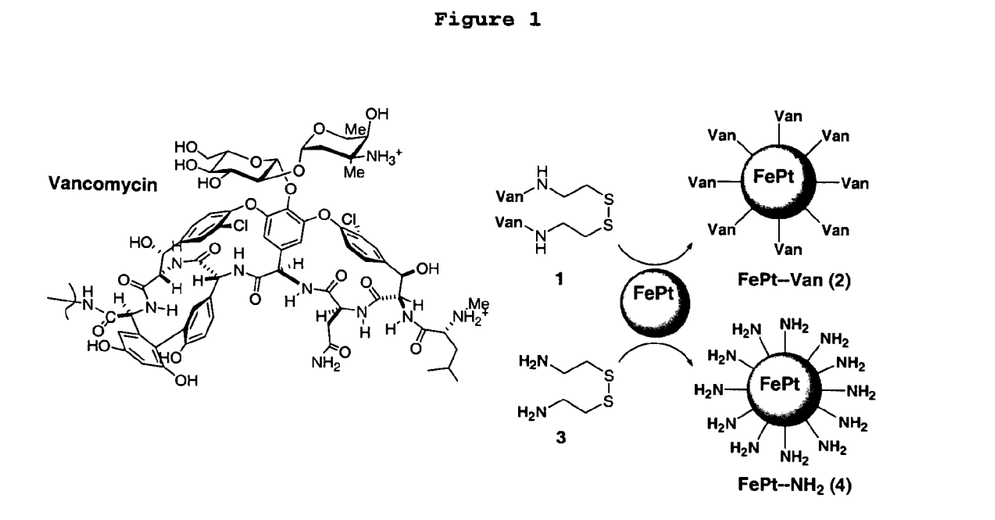
FIG. 1. An illustration shows the synthesis of Van-FePt nanoparticle 2 and control FePt nanoparticle 4 conjugates.

Synthesis of biofunctional magnetic nanoparticles: FIG. 1 illustrates the synthetic route for making the FePt—Van nanoparticles: Bis(Vancomycin) cystamide (in aqueous solution) reacts with FePt nanoparticles (in hexane phase) under vigorous stir for 12 hours to form Pt—S and Fe—S bonds that link Van to FePt. To ensure all the Vans to be completely consumed, FePt is slightly in excess. After the reaction completes, the FePt—Van nanoparticles 2 dissolve into the aqueous phase, which can be easily separated from the organic phase. The UV-vis spectrum of the aqueous solution of FePt—Van nanoparticles 2 exhibits an absorption at ~280 nm (originated from the phenyl groups of Van), indicating that Van has attached to the FePt nanoparticles. X-ray Photoelectron Spectroscopy (XPS) of the FePt—Van nanoparticles 2 shows peaks at 72.6 eV and 713/726 eV, corresponding to the energies required for breaking Pt—S and Fe—S bonds, respectively. Time-of-Flight Secondary Ion Mass spectra (ToF—SIMS) of the FePt—Van nanoparticles 2 displays mass peaks at 88 ($FeS^+$) and 1506 ($Van^+$), confirming the presence of Van on the surface of FePt. Each FePt nanoparticle has 8~9 Vans on its surface calculated according to the calibration curves generated using the solutions of Van and FePt with known concentrations. As a control, FePt nanoparticles react with cystamine (FIG. 1) to give FePt—$NH_2$ 4. The XPS of FePt—$NH_2$ 4 also displays peaks of Pt—S (72.5 eV) and Fe—S (713/726 eV) bonds, and the ToF—SIMS of FePt—$NH_2$ 4 shows mass peaks at 76 ($NH_2CH_2CH_2S^+$) and 88 ($FeS^+$), further confirming the 2-amino-ethanethiol on the surface of FePt.

Figure 2:
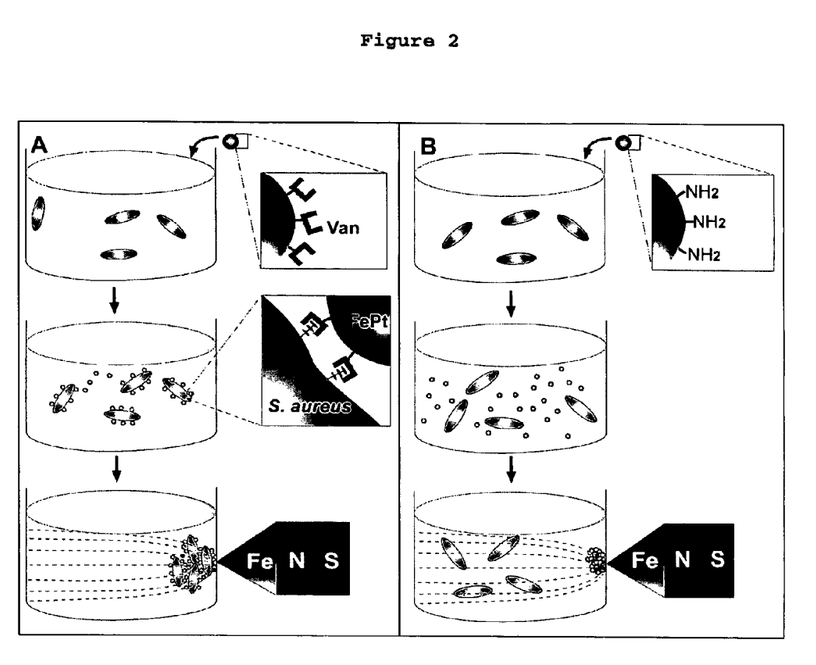

Typical experimental procedure for capture (FIG. 2): The bacteria solution was diluted to the concentration of ~10 cfu/mL in PBS buffer. FePt—Van solution was filtered through a 0.45 μm filter to eliminate the possible bacteria contamination and aggregated FePt—Van. The concentratiion of the filtrated FePt—Van solution was 11 μg/mL. 250 μl of the FePt—Van solution was added to 500 μL of the above bacteria buffer solution, and was mixed in a 1 mL vial for 0.5 minute. After standing still for 10 minutes to allow FePt—Van to attach to the surface of the bacteria, a ~400 G magnet was put outside of the vial to pull the "magnetized" bacteria to the side-wall of the vial. After applying magnetic field for another 10 minutes, solution was removed. The aggregates attracted by the magnet were washed by deionized (DI) water before being transferred for analysis by optical microscope and electron microscope.

Figure 3:
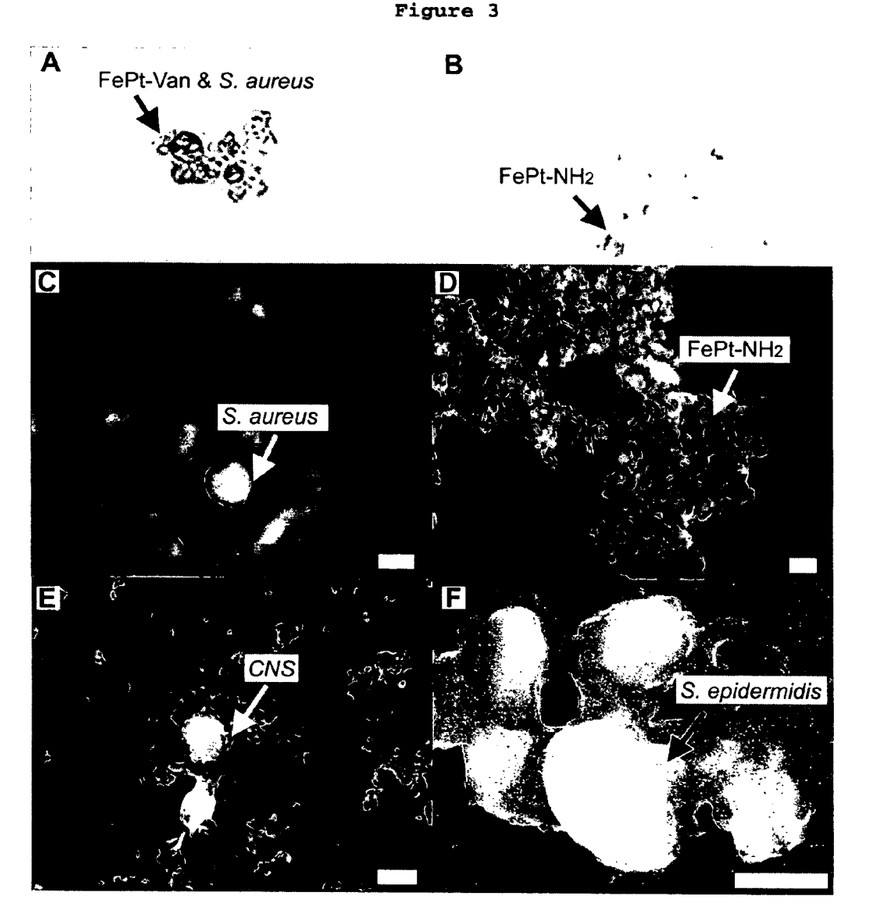

Capture of Gram Positive Bacteria:

Experimental results showed that FePt—Van nanoparticles 2 indeed captured Gram-positive strains such as *S. aureus* (8 cfu/mL), *S. epidermidis* (10 cfu/mL), and a coagulase negative staphylococci (CNS, 4 cfu/mL). FIG. 3A shows the optical image of the isolated *S. aureus* when FePt—Van nanoparticles 2 are used, and the scanning electron micrograph (SEM) confirms that these "magnetized" *S. aureus* aggregate with FePt—Van nanoparticles 2 under magnetic field (FIG. 3C). When FePt—$NH_2$4 is used, neither the optical microscopy (FIG. 3B) nor the SEM (FIG. 3D) shows *S. aureus*, suggesting that FePt—Van nanoparticles 2 bind to *S. aureus* specifically due to the molecular recognition. FePt—Van nanoparticles 2 and FePt—$NH_2$4 were used to treat solutions containing other Gram-positive strains, such as *S. epideriidis* or CNS. Experimental results showed that FePt—Van nanoparticles 2 capture both *S. epidermidis* and CNS, but FePt—$NH_2$ 4 captures neither of them, which further confirms the binding of FePt—Van nanoparticles 2 to the Gram-positive bacteria via specific interaction, similar to the case of *S. aureus*. FIGS. 3E and 3F show the SEM images of those bacteria and the aggregates of FePt—Van nanoparticles 2.

Capture of VRE Bacteria

Figure 4:
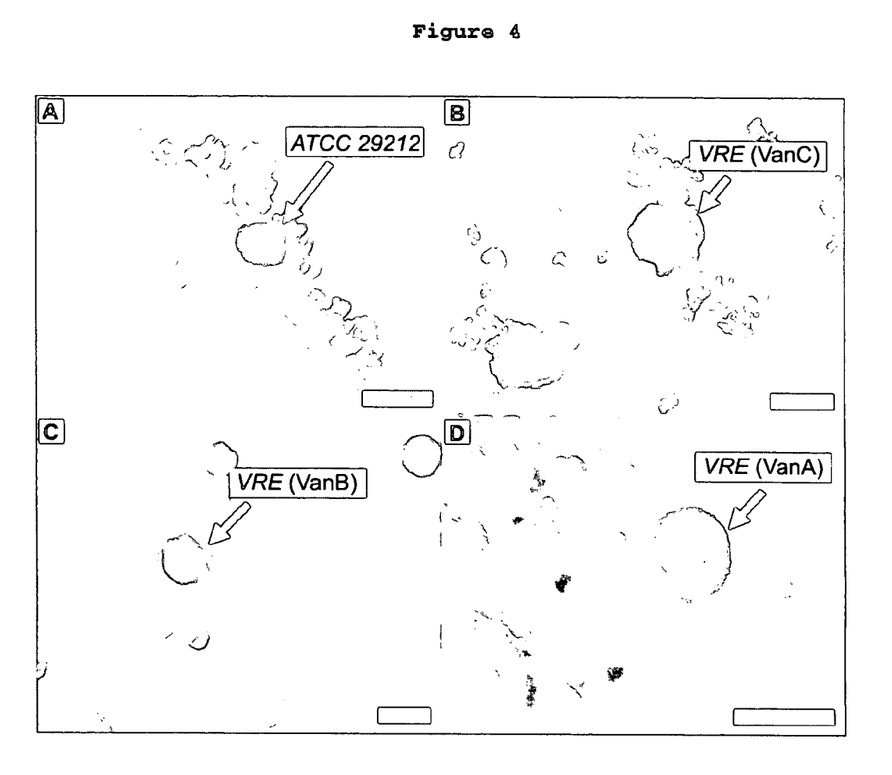

The process here is similar to the one above. Despite the fact that the affinity of Van to the terminal peptides on the cell wall of VRE decreases due to mutation,[7] previous study shows that Van-decorated gold nanoparticles[11] bind strongly to VRE. Similarly in the current experiment, FePt—Van nanoparticles 2 bind to VRE with high avidity via polyvalent interactions and captured VRE. FIG. 4 shows the SEM images of VRE or ATCC 29212 (a vancomycin sensitive strain as a positive control) that is captured by the Van-decorated FePt nanoparticles. Transmission electron microscopy also shows that FePt—Van nanoparticles 2 binds to the surface of the VRE cell. These results not only further demonstrate the effectiveness of FePt—Van nanoparticles 2 as a polyvalent ligand, but also provide a useful method to capture VRE.

Figure 5:
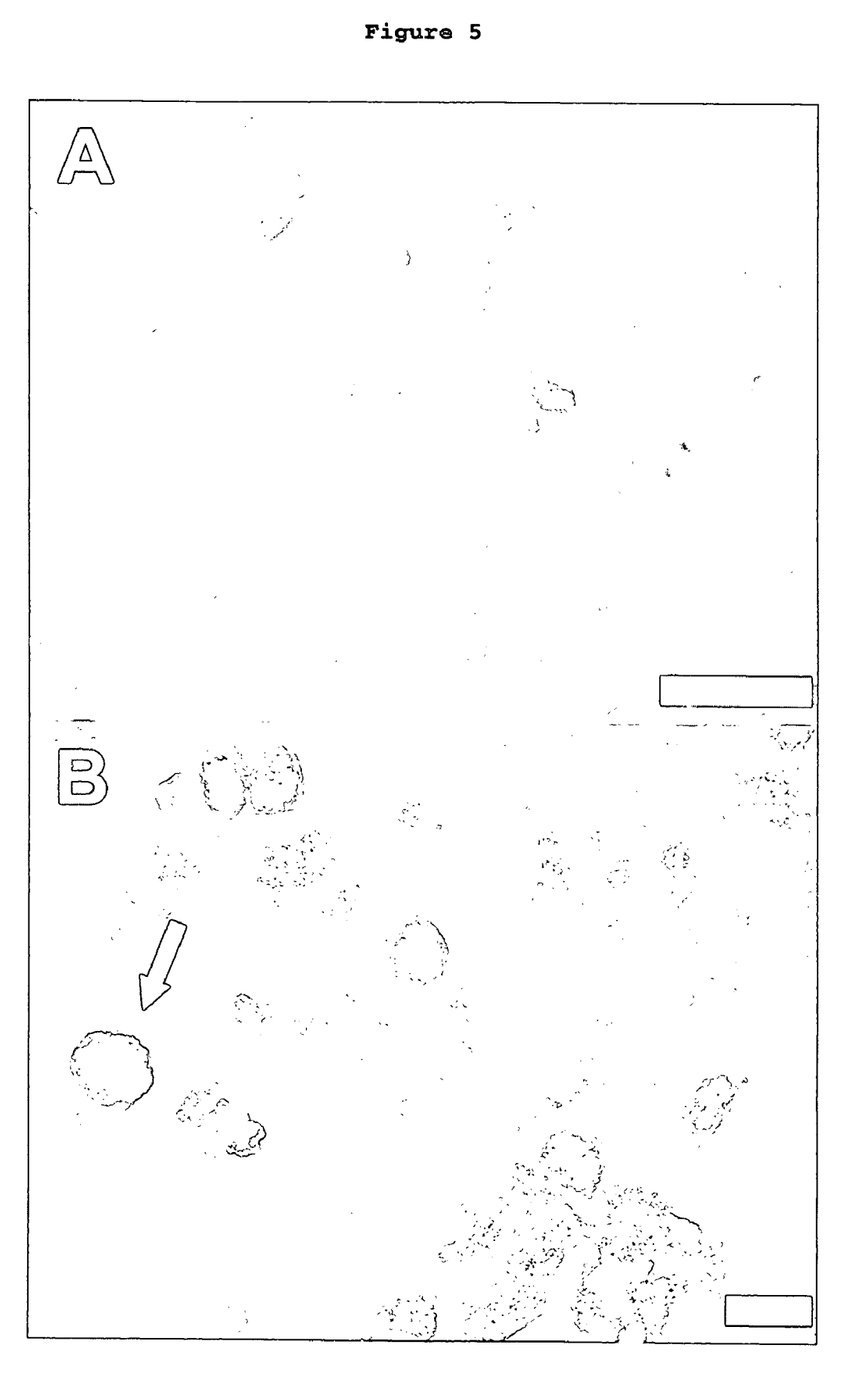

Capture bacteria in the present of WBC: After adding FePt—Van nanoparticles 2 into the solution of white blood cells (WBC, 100 cfu/mL) and following the capture experimental procedure, SEM shows only the aggregates of FePt—Van nanoparticles 2 (FIG. 5A), indicating no binding between WBC and FePt—Van nanoparticles 2. When FePt—Van nanoparticles 2 was added to the mixture of WBC (100 cfu/mL) and *S. epidermidis* (15 cfu/mL) and applied the capture procedure, SEM shows only the cells of *S. epidermidis* (FIG. 5B) and the aggregates.

Figure 6:
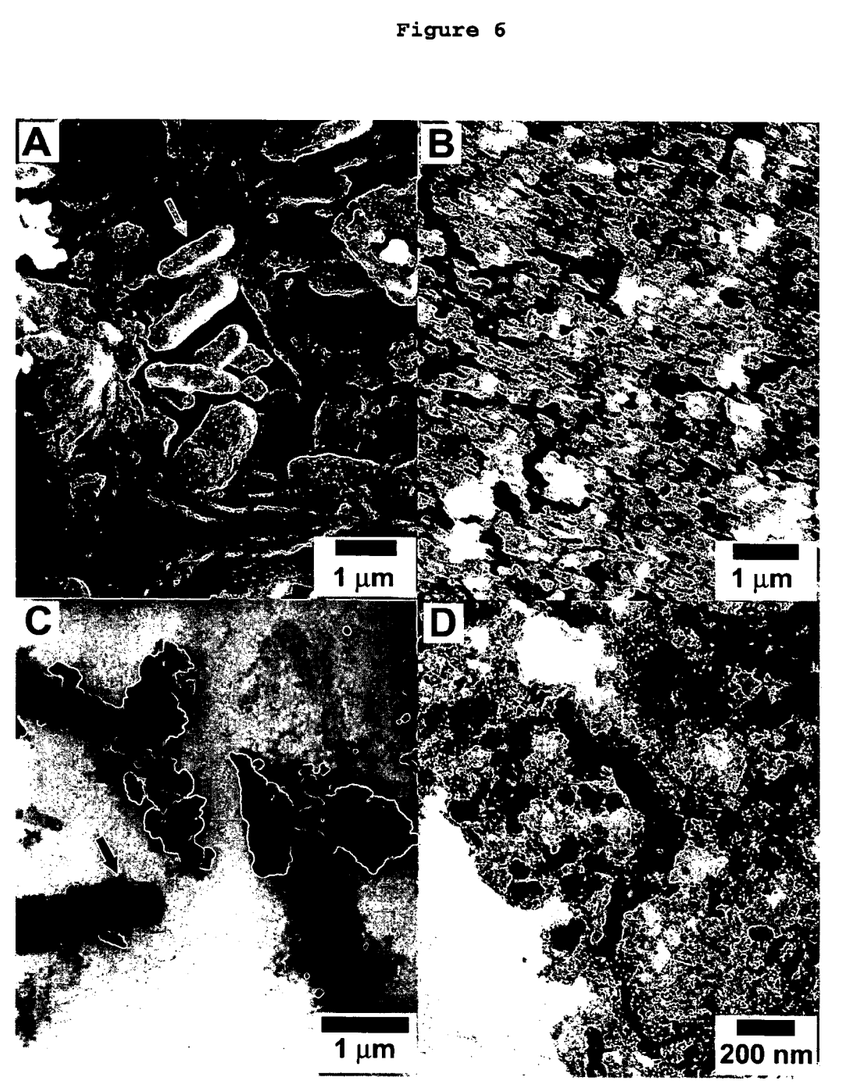
Figure 7:
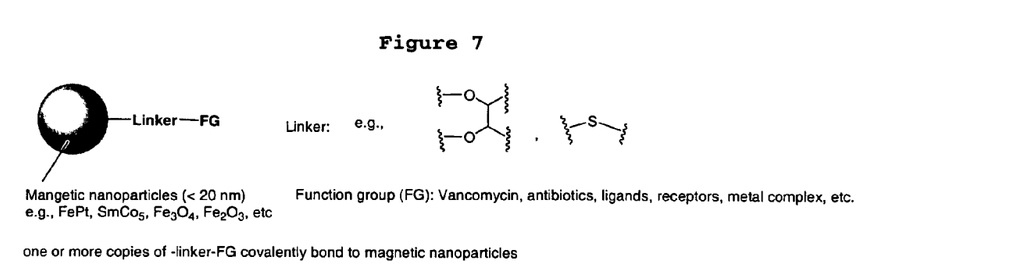
FIG. 7. An illustration shows the general structure of the biofunctional magnetic nanoparticles with one or more copies of the "-Linker-FG" (function group) covalently bonded to the magnetic nanoparticles. Magnetic nanoparticles (<20 nm) include, but are not limited to, FePt, SmCo$_5$, Fe$_3$O$_4$, Fe$_2$O$_3$, FePd, CoPt, Sm$_x$Co$_y$@Fe$_2$O$_3$, Sm$_x$Co$_y$@Fe$_3$O$_4$, M@Fe$_2$O$_3$, or M@Fe$_3$O$_4$, whereby x=1 to 4, y=5 to 20, and M is a magnetic metal selected from the group consisting of cobalt, nickel, iron, and magnetic alloys thereof. Function groups (FG) include, but is not limited to, Vancomycin (Van), antibiotics, ligands, receptors, or metal complexes.
Figure 8:
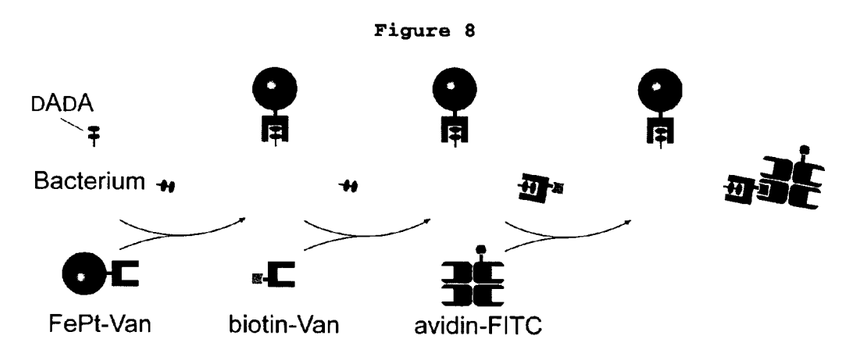
FIG. 8. A schematic illustration shows the mechanism for an on-particle fluorescence or ELISA assay.
Figure 9:
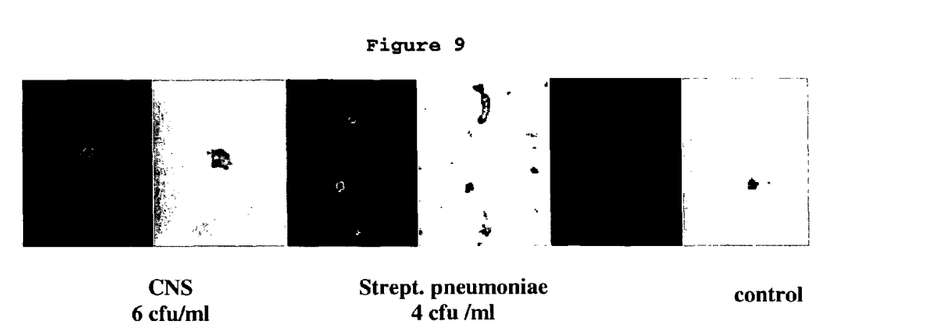
FIG. 9. The images show the results of on-particle fluorescence reporting of the presence of captured bacteria.

Capture of Gram Negative Bacteria (FIG. 6)

After adding the aqueous solution of FePt—Van nanoparticles 2 (13 µg/mL) or FePt—$NH_2$ 4 (15 µg/mL) into a vial of solution containg *E. coli* (15 cfu/mL) and shaking for 20 minutes, magnetic field (~3000 G) was applied to the solution. Upon the application of magnetic field, the magnetic nanoparticles aggregated irreversibly due to the high magnetic anisotropy of the FePt nanoparticles. Although this was sometimes an unwanted phenomena in the synthesis of magentic nanoparticles (e.g., FePt or $SmCo_5$),[3,10] it turned out to be very useful for increasing the load of magnetic nanoparticles attached to the bacteria (vide infra), thus providing adequate force to "focus" the bacteria into a small area when a small magnet is used. Then the remaining soltuion was removed and the aggregates was washed thoroughly using deionized water and transfered to a glass slide for microscopic study.

REFERENCES (1) Wagner, S. J.; Robinette, D. *Transfusion* 1998, 38, 674-679; Che, Y. H.; Li, Y. B.; Slavik, M.; Paul, D. *J. Food Protection* 2000, 63, 1043-1048.

(2) Puntes, V. F.; Krishnan, K. M.; Alivisatos, A. P. *Science* 2001, 291, 2115-2117; Weller, D.; Moser, A. *IEEE Trans. Magn.* 1999, 35, 4423-4439; Osterloh, F. E. *J. Am. Chem. Soc.* 2002, 124, 6248-6249; Zhang, Z. J.; Wang, Z. L.; Chakoumakos, B. C.; Yin, J. S. *J. Am. Chem. Soc.* 1998, 120, 1800-1804; Tripp, S. L.; Pusztay, S. V.; Ribbe, A. E.; Wei, A. *J. Am. Chem. Soc.* 2002, 124, 7914-7915; Park, J. I.; Cheon, J. *J. Am. Chem. Soc.* 2001, 123, 5743-5746; Majetich, S. A.; Artman, J. O.; McHenry, M. E.; Nuhfer, N. T.; Staley, S. W. *Phys. Rev. B* 1993, 48, 16845-16848; Sun, S. H.; Anders, S.; Hamann, H. F.; Thiele, J. U.; Baglin, J. E. E.; Thomson, T.; Fullerton, E. E.; Murray, C. B.; Terris, B. D. *J. Am. Chem. Soc.* 2002, 124, 2884-2885.

(3) Sun, S. H.; Murray, C. B.; Weller, D.; Folks, L.; Moser, A. *Science* 2000, 287, 1989-1992.

(4) Josephson, L.; Kircher, M. F.; Mahmood, U.; Tang, Y.; Weissleder, R. *Bioconjugate Chem.* 2002, 13, 554-560.

(5) Perez, J. M.; O'Loughin, T.; Simeone, F. J.; Weissleder, R.; Josephson, L. *J. Am. Chem. Soc.* 2002, 124, 2856-2857; Josephson, L.; Perez, J. M.; Weissleder, R. *Angew. Chem. Int. Ed.* 2001, 40, 3204-3206; Dyal, A.; Loos, K.; Noto, M.; Chang, S. W.; Spagnoli, C.; Shafi, K.; Ulman, A.; Cowman, M.; Gross, R. A. *J. Am. Chem. Soc.* 2003, 125, 1684-1685; Lewin, M.; Carlsso, N.; Tung, C. H.; Tang, X. W.; Cory, D.; Scadden, D. T.; Weissleder, R. *Nature Biotech.* 2000, 18, 410-414; Safarik, I.; Safarikova, M. *Mon. Chem.* 2002, 133, 737-759; Perez, J. M.; Simeone, F. J.; Saeki, Y.; Josephson, L.; Weissleder, R. *J. Am. Chem. Soc.* 2003, 125, 10192-10193.

(6) Mammen, M.; Choi, S. K.; Whitesides, G. M. *Angew. Chem. Int. Ed.* 1998, 37, 2755-2794.

(7) Walsh, C. Antibiotics: actions, origins, resistance; 1st ed.; ASM press: Washington, D.C., 2003.

(8) Walsh, C. *Science* 1999, 284, 442-443; Fan, C.; Moews, P. C.; Walsh, C. T.; Knox, J. R. *Science* 1994, 266, 439-443; Xing, B.; Yu, C.-W.; Chow, K.-H.; Ho, P.-L.; Fu, D.; Xu, B. *J. Am. Chem. Soc.* 2002, 124, 14846-14847.

(9) Rao, J.; Yan, L.; Xu, B.; Whitesides, G. M. *J. Am. Chem. Soc.* 1999, 121, 2629-2630; Rao, J. H.; Lahiri, J.; Isaacs, L.; Weis, R. M.; Whitesides, G. M. *Science* 1998, 280, 708-711.

(10) Gu, H.; Xu, B.; Rao, J.; Zheng, R. K.; Zhang, X. X.; Fung, K. K.; Wong, C. Y. C. *J. Appl. Phys.* 2003, 95, 7589-7591.

(11) Gu, H.; Ho, P. L.; Tong, E.; Wang, L.; Xu, B. *Nano. Lett.* 2003, 3, 1261-1263.

What is claimed is:

1. A method of detecting a microorganism in a sample, comprising the steps of:
    (a) contacting biofunctional magnetic nanoparticles having a biofunctional group with a sample to be tested for possible presence of a microorganism, wherein the biofunctional group is an antibiotic;
    (b) using a magnetic field to aggregate said biofunctional magnetic nanoparticles; and
    (c) detecting presence of a complex between said microorganism and said biofunctional magnetic nanoparticle after said biofunctional magnetic nanoparticles being aggregated in step(b), wherein presence of said complex indicates presence of said microorganism in the sample.

2. The method of claim 1, wherein the biofunctional magnetic nanoparticles are capable of engaging in ligand-receptor interaction.

3. The method of claim 1, wherein the magnetic nanoparticles are alloys.

4. The method of claim 1, wherein the antibiotic is vancomycin (Van).

5. The method of claim 1, wherein the sample is a solid, liquid, or gas.

6. The method of claim 1, wherein the microorganism is a bacterium.

7. The method of claim 1, wherein detection involves analysis with an optical microscope.

8. The method of claim 1, wherein said method detects a microorganism at a concentration of at least as low as 10 colony forming units (cfu) in one milliliter of solution.

9. The method of claim 1, wherein said method detects a microorganism at a concentration of at least as low as 4 colony forming units (cfu) in one milliliter of solution.

10. The method of claim 3, wherein the alloys contain platinum.

11. The method of claim 3, wherein the magnetic nanoparticles are $SmCo_5$.

12. The method of claim 6, wherein the bacterium is Gram positive or Gram negative.

13. The method of claim 12, wherein the bacterium is Vancomycin Resistant Enterococci.

* * * * *